United States Patent
Litvak

(10) Patent No.: US 8,965,519 B2
(45) Date of Patent: *Feb. 24, 2015

(54) ENCODING FINE TIME STRUCTURE IN PRESENCE OF SUBSTANTIAL INTERACTION ACROSS AN ELECTRODE ARRAY

(71) Applicant: Advanced Bionics AG, Staefa (CH)

(72) Inventor: Leonid Michael Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/082,725

(22) Filed: Nov. 18, 2013

(65) Prior Publication Data

US 2014/0074184 A1 Mar. 13, 2014

Related U.S. Application Data

(63) Continuation of application No. 11/845,673, filed on Aug. 27, 2007, now Pat. No. 8,600,515, which is a continuation-in-part of application No. 10/981,944, filed on Nov. 5, 2004, now Pat. No. 7,277,760.

(51) Int. Cl.
*A61N 5/00* (2006.01)
*A61N 1/36* (2006.01)
*H04R 25/00* (2006.01)

(52) U.S. Cl.
CPC ............ *A61N 1/36032* (2013.01); *H04R 25/50* (2013.01)
USPC ............................................................ 607/56

(58) Field of Classification Search
CPC ............................. A61N 1/36032; A61F 11/04
USPC .......................................... 607/56, 55, 57, 60
See application file for complete search history.

(56) References Cited

U.S. PATENT DOCUMENTS

| 3,751,605 A | 8/1973 | Michelson |
|---|---|---|
| 4,400,590 A | 8/1983 | Michelson |

(Continued)

FOREIGN PATENT DOCUMENTS

| WO | 00/01200 A1 | 1/2000 |
|---|---|---|
| WO | 02/09808 A1 | 2/2002 |

(Continued)

OTHER PUBLICATIONS

Eddington et al. Auditory prostheses research with multiple channel intracochlear stimulation in man. Ann Otol Rhinol Laryngo l. Nov.-Dec. 1978;87(6 Pt 2):1-39.*

(Continued)

*Primary Examiner* — Christopher D Koharski
*Assistant Examiner* — Jeremiah Kimball
(74) *Attorney, Agent, or Firm* — Wong, Cabello, Lutsch, Rutherford & Brucculeri LLP.

(57) ABSTRACT

Among other things, a stimulation strategy can be customized for a cochlear implant implanted in an individual by testing at least a pair of electrodes selected from an array of electrodes associated with the cochlear implant. Testing the at least a pair of electrodes includes applying a first stimulation to the at least a pair of electrodes using a first pair of pulse trains that are out of phase, and applying a second stimulation to the at least a pair of electrodes using a second pair of pulse trains that are out of phase. A determination is made on whether the at least a pair of electrodes stimulate the same neural population based on a sensitivity of the individual to detect a perceived difference between the two pairs of pulse trains. The one or more electrodes of the array of electrodes are selectively stimulated based on the determination.

18 Claims, 13 Drawing Sheets

(56) References Cited

U.S. PATENT DOCUMENTS

| | | | |
|---|---|---|---|
| 4,495,384 | A | 1/1985 | Scott et al. |
| 4,819,647 | A | 4/1989 | Byers et al. |
| 5,479,522 | A | 12/1995 | Lindemann et al. |
| 5,601,617 | A | 2/1997 | Loeb et al. |
| 5,603,726 | A | 2/1997 | Schulman et al. |
| 5,626,629 | A | 5/1997 | Faltys et al. |
| 5,721,783 | A | 2/1998 | Anderson |
| 5,776,172 | A | 7/1998 | Schulman et al. |
| 5,824,022 | A | 10/1998 | Zilberman et al. |
| 5,876,425 | A | 3/1999 | Gord et al. |
| 5,938,691 | A | 8/1999 | Schulman et al. |
| 5,991,419 | A | 11/1999 | Brander |
| 6,002,966 | A | 12/1999 | Loeb et al. |
| 6,052,624 | A | 4/2000 | Mann |
| 6,067,474 | A | 5/2000 | Schulman et al. |
| 6,078,838 | A | 6/2000 | Rubinstein |
| 6,129,753 | A | 10/2000 | Kuzma |
| 6,157,861 | A | 12/2000 | Faltys et al. |
| 6,181,969 | B1 | 1/2001 | Gord |
| 6,195,585 | B1 | 2/2001 | Karunasiri et al. |
| 6,205,360 | B1 | 3/2001 | Carter et al. |
| 6,208,882 | B1 | 3/2001 | Lenarz et al. |
| 6,219,580 | B1 | 4/2001 | Faltys et al. |
| 6,249,704 | B1 | 6/2001 | Maltan et al. |
| 6,272,382 | B1 | 8/2001 | Faltys et al. |
| 6,289,247 | B1 | 9/2001 | Faltys et al. |
| 6,295,467 | B1 | 9/2001 | Kollmeier et al. |
| 6,393,325 | B1 | 5/2002 | Mann et al. |
| 6,415,185 | B1 | 7/2002 | Maltan |
| 6,449,372 | B1 | 9/2002 | Greminger |
| 6,516,227 | B1 | 2/2003 | Meadows et al. |
| 6,549,633 | B1 | 4/2003 | Westermann |
| 6,565,503 | B2 * | 5/2003 | Leysieffer et al. ............... 600/25 |
| 2003/0036782 | A1 | 2/2003 | Hartley et al. |
| 2004/0082980 | A1 | 4/2004 | Mouine et al. |
| 2004/0136556 | A1 | 7/2004 | Litvak et al. |
| 2004/0193230 | A1 | 9/2004 | Overstreet |
| 2005/0107844 | A1 * | 5/2005 | Van Den Honert et al. ..... 607/57 |
| 2005/0137650 | A1 | 6/2005 | Litvak et al. |
| 2005/0137651 | A1 | 6/2005 | Litvak et al. |
| 2005/0192648 | A1 * | 9/2005 | Killian et al. .................... 607/57 |
| 2006/0195160 | A1 * | 8/2006 | Blamey et al. ................... 607/57 |
| 2006/0235490 | A1 * | 10/2006 | Killian et al. .................... 607/60 |

FOREIGN PATENT DOCUMENTS

| | | |
|---|---|---|
| WO | 03/015863 A2 | 2/2003 |
| WO | 2004/043537 A1 | 5/2004 |
| WO | 2005/053358 A1 | 6/2005 |

OTHER PUBLICATIONS

Zeng et al. Cochlear Implants: Auditory Prostheses and Electric Hearing. Springer: Apr. 21, 2004; ISBN 978-0-387.*

Eddington et al. Auditory prostheses research with multiple channel intracochlear stimulation in man. Ann Otol Rhinal Laryngol. Nov.-Dec. 1978; 87(6 Pt 2): 1-39.

Douek et al., "A New Approach to the Cochlear Implant," Proc. Roy. Soc. Med. 70:379-383 (Jun. 1977).

Harnsberger, et al., "Perceptual 'vowel spaces' of Cochlear Implant Users: Implications for the Study of Auditory Adaptation to Spectral Shift." J Acoust Soc Am, 109(5 Part 1 ): 2135-2145 (May 2001).

Loizon, P.C., "Mimicking the Human Ear," IEEE Signal Processing Magazine, pp. 101-130 (Sep. 1998).

McDermott, H.J. and and C.M. McKay, "Pitch Ranking with Nonsimultaneous Dual-Electrode Electrical Stimulation of the Cochlea," J Acoust Soc Am 96(1): 155-162 (1994).

Morse, R.P. and G. F. Meyer, "The practical Use of Noise to Improve Speech Coding by Analogue Cochlear Implants," Chaos, Solutions and Fractals, 11(12): 1885-1894 (2000).

Rubinstein et al., "The Neurophysiological Effects of Simulated Auditory Prosthesis Simulation" Second Quarterly Progress Report N01-DC-6-2111, Department of Otolaryngology—Head and Neck Surgery, The University of Iowa College of Medicine, Iowa City, IA 52242, pp. 1-12 (May 27, 1997).

Scheirer, et al., "Construction and Evaluation of Robust Multifeature Speech/Music Discriminator", 1997 IEEE International Conference on Acoustics, Speech, and Signal Processing: Apr. 21-24, 1997, Munich, Germany; Los Alamitos, California.: IEEE Computer Society Press, pp. 1331-1334 (1997).

Smith, et al., "Chimaeric Sounds Reveal Dichotomies in Auditory Perception," Nature 416 (6876): 87-90 (Mar. 7, 2002).

van Wieringen and J. Wouters, "Comparison of Procedures to Determine Electrical Stimulation Thresholds in Cochlear Implant Users," Ear and Hearing, 22(6): 528-538 (2001).

Zeng, et al., "Cochlear Implants: Auditory Prostheses and Electric Hearing." Springer: Apr. 21, 2004; ISBN 978-0-387-40646-6 (pp. 312-315).

Zeng, et al., "Loudness of Simple and Complex Stimuli in Electric Hearing," Annals of Otology, Rhinology & Laryngology, 104(9):235-238 (1995).

Zhang, et al., "Loudness of Dynamic Stimuli in Acoustic and Electric Hearing," J Acoust Soc Am, 102(5 Part 1): 2925-2934 (Nov. 1997).

* cited by examiner

ENCODING FINE TIME STRUCTURE IN PRESENCE OF SUBSTANTIAL INTERACTION ACROSS AN ELECTRODE ARRAY

CROSS-REFERENCE TO RELATED APPLICATIONS

This application is a continuation of U.S. patent application Ser. No. 11/845,673 (now U.S. Pat. No. 8,600,515), filed Aug. 27, 2007, which is a continuation-in-part of U.S. patent application Ser. No. 10/981,944, filed Nov. 5, 2004 (now U.S. Pat. No. 7,277,760). Priority is claimed to all of these applications, and all are incorporated herein by reference in their entireties.

TECHNICAL FIELD

This disclosure relates to, systems and methods for stimulating the cochlea, for example, systems and methods for encoding the fine time structure components of a sound signal in the presence of substantial interaction across an electrode array.

BACKGROUND

Prior to the past several decades, scientists generally believed that it was impossible to restore hearing to the deaf. However, scientists have had increasing success in restoring normal hearing to the deaf through electrical stimulation of the auditory nerve. The initial attempts to restore hearing were not very successful, as patients were unable to understand speech. However, as scientists developed different techniques for delivering electrical stimuli to the auditory nerve, the auditory sensations elicited by electrical stimulation gradually came closer to sounding more like normal speech. The electrical stimulation is implemented through a prosthetic device, called cochlear implant, which is implanted in the inner ear to restore partial hearing to profoundly deaf people.

Such cochlear implants generally employ an electrode array that is inserted in the cochlear duct, usually in the scala tympani. One or more electrodes of the array selectively stimulate different auditory nerves at different places in the cochlea based on the pitch of a received sound signal. Within the cochlea, there are two main cues that convey "pitch" (frequency) information to the patient. There are (1) the place or location of stimulation along the length of a cochlear duct and (2) the temporal structure of the stimulating waveform. In the cochlea, sound frequencies are mapped to a "place" in the cochlea, generally from low to high sound frequencies mapped from the apical to basilar direction. The electrode array is fitted to the patient to arrive at a mapping scheme such that electrodes near the base of the cochlea are stimulated with high frequency signals, while electrodes near the apex are stimulated with low frequency signals.

The position of each electrode is not very precise. That is, there are only a limited number of electrodes, e.g., numbering about 16 to 24 electrodes, spread along the length of the electrode array, inserted into one of the spiraling ducts of the cochlea. Hence, accurately mapping to a "place" within the cochlea can be difficult, as the mapping is limited by the resolution of the discretely placed electrodes.

In a conventional cochlear implant, an envelope is extracted in each channel, and the remaining information, i.e., fine structure, is discarded. Given the number of channels in current processors, information in the fine structure can be very important for hearing certain sounds, particularly music. In previous disclosures, methods for encoding the fine time structure have been proposed. In these methods, stimulation is presented on one or more virtual or physical channels that has been optimally selected based on the estimate of the fine structure in each analysis band. However, these methods do not take into account the recent findings that non-simultaneous stimulation of nearby physical or virtual electrodes is perceived as a single pitch. For example, if in one band, the desired stimulation location is that corresponding to 1000 Hz, and in an adjacent band the desired location corresponds to 1300 Hz, then if both are present, the subject might perceive a pitch corresponding to 1150 Hz. This is known as decreased resolution, and it has a negative impact on the performance of current implants that seek to improve hearing by increasing the number of electrodes or using virtual electrodes to increase the number places to stimulate on a cochlea.

SUMMARY

The present inventors recognized a need to improve the functionality of newer generation implants that utilize increased numbers of electrodes or virtual electrodes. Disclosed are methods and systems for reducing the effects of decreased resolution in a cochlear implant, for example, by encoding the fine time structure of sound signals in the presence of substantial interaction across an electrode array.

In one aspect, a method of reducing the effects of decreased resolution in a cochlear implant includes analyzing an incoming sound within a plurality of frequency bands. One or more dominant components in each frequency band is estimated. The dominant components are analyzed to determine if any two or more are within a resolution region of one another. Of any two or more components that are within a resolution region of one another, the component with the lesser associated energy is removed, thereby producing a sound signal with a reduced pattern of components. The reduced pattern signal is transmitted to an array of electrodes associated with a cochlear implant.

In another aspect, a cochlear stimulation system includes a plurality of analysis channels. Each channel has a filter associated with a frequency band. A processor is in communication with the plurality of analysis channels. The processor estimates the dominant components in each frequency band. The system also includes means for analyzing the dominant components and determining if any two or more are within a resolution region of one another. Additionally, the system includes means for removing the component that has lesser associated energy of two or more components that are within a resolution region of one another, thereby producing a sound signal with a reduced pattern of components.

In another aspect, a method of reducing the effects of decreased resolution in a cochlear implant includes determining the value of an individual's resolution region. A plurality of dominant components within a sound signal are analyzed. A component that has lesser associated energy of two or more components that are within the resolution region of one another is removed, thereby producing a sound signal with a reduced pattern of components. The reduced pattern signal is transmitted to an array of electrodes associated with the cochlear implant.

In another aspect, a method for estimating a resolution region associated with a cochlear implant used by an individual includes providing a first sound having a predetermined frequency. A second sound in close succession to the first sound is provided. The second sound has a predetermined frequency different from the first sound. It is determined if the individual hears two sounds. These steps are repeated until it is determined that the individual does not hear two separate sounds. The second sound has a frequency closer to the frequency of the first sound upon each consecutive repetition of the above steps.

In another aspect, a stimulation strategy can be customized for a cochlear implant implanted in an individual by testing at least a pair of electrodes selected from an array of electrodes associated with the cochlear implant. Testing the at least a pair of electrodes includes applying a first stimulation to the at least a pair of electrodes using a first pair of pulse trains that are out of phase, and applying a second stimulation to the at least a pair of electrodes using a second pair of pulse trains that are out of phase. A determination is made on whether the at least a pair of electrodes stimulate the same neural population based on a sensitivity of the individual to detect a perceived difference between the two pairs of pulse trains. The one or more electrodes of the array of electrodes are selectively stimulated based on the determination.

Implementations can optionally include one or more of the following features. The sensitivity of the individual can be determined using a psychophysical method. The at least a pair of electrodes can be selectively not stimulated when detected that the at least a pair of electrodes stimulate the same neural population.

In another aspect, a stimulation strategy can be customized for a cochlear implant implanted in an individual by determining an excitation pattern for at least a first electrode and a second electrode selected from an array of electrodes associated with the cochlear implant. Determining the excitation pattern includes applying a masking stimulus and a probing stimulus separated by a time delay to each electrode, and determining an ability of the individual to distinguish the masking and probing stimuli. The excitation pattern for the first electrode can be compared against the excitation pattern for the second electrode. Based on the comparison, the one or more electrodes of the array of electrodes is selectively stimulating.

Implementations can optionally include one or more of the following features. The ability of the individual to distinguish the masking and probing stimuli can be determined using a psychophysical method. Also, the excitation patterns for the first and second electrodes can be compared to determine whether the excitation pattern for the first electrode overlaps with the excitation pattern for the second electrode. When detected that the excitation pattern for the first electrode overlaps with the excitation pattern for the second electrode, the first and second electrodes can be selectively not stimulated. In some instances, the tests for independence of two or more electrodes can be encoded using an implantable device (e.g., implantable cochlear stimulator alone or together with a speech processor.)

The subject matter described in this specification can be implemented as a method or as a system or using computer program products, tangibly embodied in information carriers, such as a CD-ROM, a DVD-ROM, a semiconductor memory, and a hard disk. Such computer program products may cause a data processing apparatus to conduct one or more operations described in this specification.

In addition, the subject matter described in this specification can also be implemented as a system including a processor and a memory coupled to the processor. The memory may encode one or more programs that cause the processor to perform one or more of the method acts described in this specification. Further the subject matter described in this specification can be implemented using various data processing machines.

The details of one or more embodiments are set forth in the accompanying drawings and the description below. Other features and advantages will be apparent from the description and drawings, and from the claims.

DESCRIPTION OF DRAWINGS

These and other features and advantages will be apparent from the following more particular description thereof, presented in conjunction with the following drawings, wherein.

Like reference symbols in the various drawings indicate like elements.

DETAILED DESCRIPTION

Disclosed are systems and methods for encoding the fine time structure of sound signals in the presence of substantial interaction across an electrode array associated with a cochlear implant. An overview of the structure and functionality of an exemplary cochlear implant system is provided below in connection with the description of FIGS. 1, 2A and 2B. The following description is exemplary and the device and methods described herein can be used with other types and other configurations of cochlear implant systems.

Figure 1:
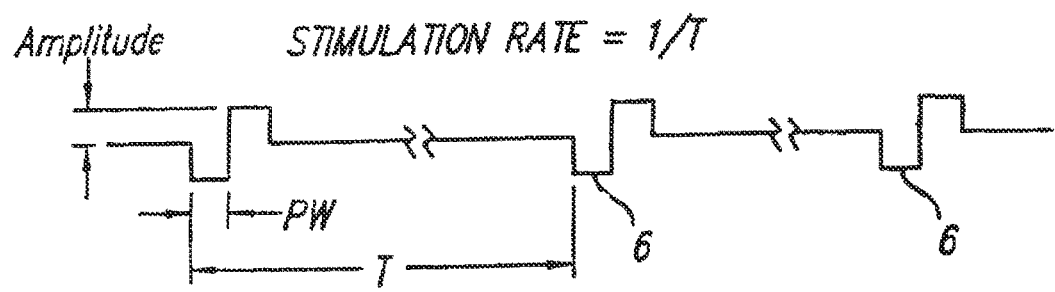
FIG. 1 is a current stimulation waveform that defines the stimulation rate (1/T) and biphasic pulse width (PW) associated with electrical stimuli, as those terms are commonly used in the neurostimulation art.

FIG. 1 shows a waveform diagram of a biphasic pulse train. The figure defines stimulation rate (1/T), pulse width (PW) and pulse amplitude as those terms are commonly used in connection with a neurostimulator device, such as a cochlear implant, a spinal cord stimulator (SCS), a deep brain stimulator (DBS), or other neural stimulator. All such systems commonly generate biphasic pulses 6 of the type shown in FIG. 1 in order to deliver stimulation to tissue.

A "biphasic" pulse 6 consists of two pulses: a first pulse of one polarity having a specified magnitude, followed immediately or after a very short delay by a second pulse of the opposite polarity, although possibly of different duration and amplitude, such that the total charge of the first pulse equals the total charge of the second pulse. It is thought that such charge-balancing can prevent damage to stimulated tissue and prevent electrode corrosion. For multichannel cochlear stimulators, it is common to apply a high rate biphasic stimulation pulse train to each of the pairs of electrodes in the implant (described below) in accordance with a selected strategy and modulate the pulse amplitude of the pulse train as a function of information contained within the sensed acoustic signal.

Figure 2A:
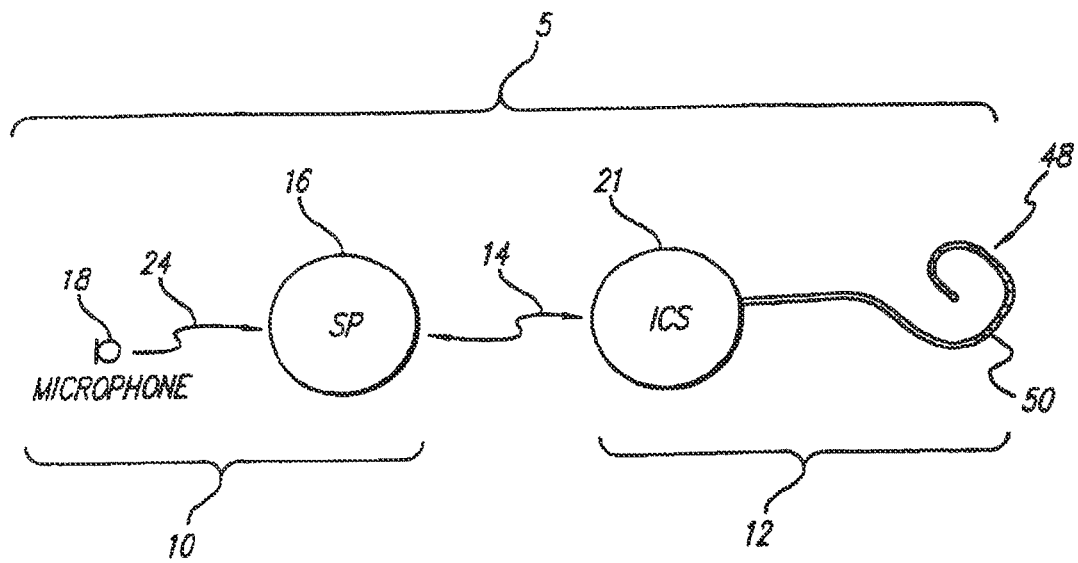
FIGS. 2A and 2B, respectively, show a cochlear implant system and a partial functional block diagram of the cochlear stimulation system, which system is capable of providing high rate pulsatile electrical stimuli and virtual electrodes FIG. 3A schematically illustrates the locations of applied stimuli within a duct of the cochlea, without the benefit of virtual electrodes.

FIG. 2A shows a cochlear stimulation system 5 that includes a speech processor portion 10 and a cochlear stimulation portion 12. The speech processor portion 10 includes a speech processor (SP) 16 and a microphone 18. The microphone 18 may be connected directly to the SP 16 or coupled to the SP 16 through an appropriate communication link 24. The cochlear stimulation portion 12 includes an implantable cochlear stimulator (ICS) 21 and an electrode array 48. The electrode array 48 is adapted to be inserted within the cochlea of a patient. The array 48 includes a plurality of electrodes 50, e.g., sixteen electrodes, spaced along the array length and which electrodes are selectively connected to the ICS 21. The electrode array 48 may be substantially as shown and described in U.S. Pat. No. 4,819,647 or 6,129,753, both patents incorporated herein by reference. Electronic circuitry within the ICS 21 allows a specified stimulation current to be applied to selected pairs or groups of the individual electrodes included within the electrode array 48 in accordance with a specified stimulation pattern defined by the SP 16.

The ICS 21 and the SP 16 are shown in FIG. 2A as being linked together electronically through a suitable data or communications link 14. In some cochlear implant systems, the SP 16 and microphone 18 comprise the external portion of the cochlear implant system and the ICS 21 and electrode array 48 comprise the implantable portion of the system. Thus, the data link 14 is a transcutaneous (through the skin) data link that allows power and control signals to be sent from the SP 16 to the ICS 21. In some embodiments, data and status signals may also be sent from the ICS 21 to the SP 16.

Certain portions of the cochlear stimulation system 5 can be contained in a behind the ear (BTE) unit that is positioned at or near the patient's ear. For example, the BTE unit can include the SP 16 and a battery module, which are coupled to a corresponding ICS 21 and an electrode array 48. A pair of BTE units and corresponding implants can be communicatively linked via a Bionet System and synchronized to enable bilateral speech information conveyed to the brain via both the right and left auditory nerve pathways. The Bionet system uses an adapter module that allows two BTE units to be synchronized both temporally and tonotopically in order to maximize a patient's listening experience.

Figure 2B:
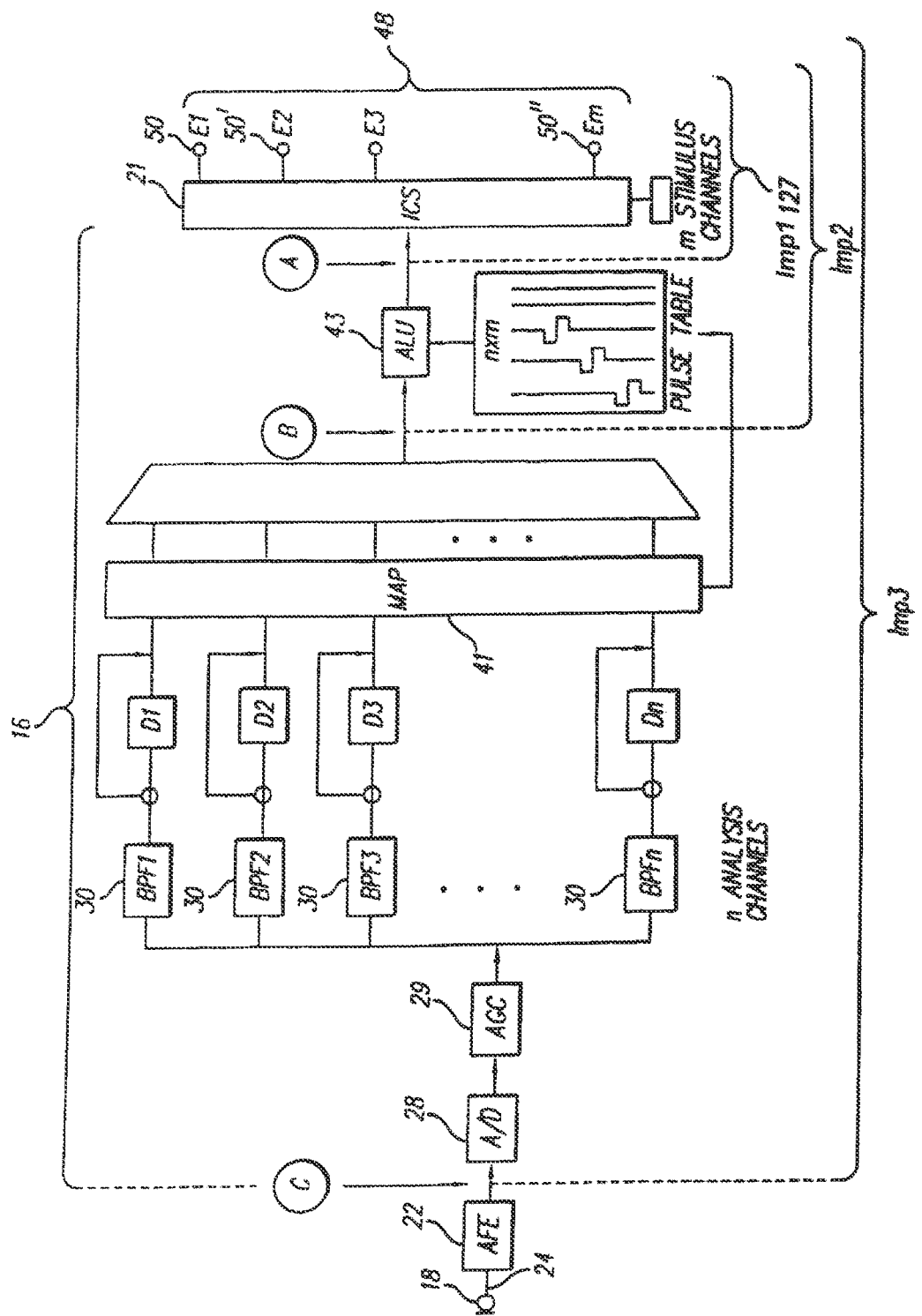

FIG. 2B shows a partial block diagram of one embodiment of a cochlear implant system capable of providing a high pulsatile stimulation pattern and virtual electrodes, which are described below. At least certain portions of the SP 16 can be included within the implantable portion of the overall cochlear implant system, while other portions of the SP 16 can remain in the external portion of the system. In general, at least the microphone 18 and associated analog front end (AFE) circuitry 22 can be part of the external portion of the system and at least the ICS 21 and electrode array 48 can be part of the implantable portion of the system. As used herein, the term "external" means not implanted under the skin or residing within the inner ear. However, the term "external" can also mean residing within the outer ear, residing within the ear canal or being located within the middle ear.

Typically, where a transcutaneous data link must be established between the external portion and implantable portions of the system, such link is implemented by using an internal antenna coil within the implantable portion, and an external antenna coil within the external portion. In operation, the external antenna coil is aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments, both the SP 16 and the ICS 21 may be implanted within the patient, either in the same housing or in separate housings. If in the same housing, the link 14 may be implemented with a direct wire connection within such housing. If in separate housings, as described, e.g., in U.S. Pat. No. 6,067,474, incorporated herein by reference, the link 14 may be an inductive link using a coil or a wire loop coupled to the respective parts.

The microphone 18 senses sound waves and converts such sound waves to corresponding electrical signals and thus functions as an acoustic transducer. The electrical signals are sent to the SP 16 over a suitable electrical or other link 24. The SP 16 processes these converted acoustic signals in accordance with a selected speech processing strategy to generate appropriate control signals for controlling the ICS 21. Such control signals specify or define the polarity, magnitude, location (which electrode pair or electrode group receive the stimulation current), and timing (when the stimulation current is applied to the electrode pair) of the stimulation current that is generated by the ICS. Such control signals thus combine to produce a desired spatio-temporal pattern of electrical stimuli in accordance with a desired speech processing strategy.

A speech processing strategy is used, among other reasons, to condition the magnitude and polarity of the stimulation current applied to the implanted electrodes of the electrode array 48. Such speech processing strategy involves defining a pattern of stimulation waveforms that are to be applied to the electrodes as controlled electrical currents.

FIG. 2B depicts the functions that are carried out by the SP 16 and the ICS 21. It should be appreciated that the functions shown in FIG. 2B (dividing the incoming signal into frequency bands and independently processing each band) are representative of just one type of signal processing strategy that may be employed. Other signal processing strategies could just as easily be used to process the incoming acoustical signal. A description of the functional block diagram of the cochlear implant shown in FIG. 2B is found in U.S. Pat. No. 6,219,580, incorporated herein by reference. The system and method described herein may be used with other cochlear systems other than the system shown in FIG. 2B, which system is not intended to be limiting.

The cochlear implant functionally shown in FIG. 2B provides n analysis channels that may be mapped to one or more stimulus channels. That is, after the incoming sound signal is received through the microphone 18 and the analog front end circuitry (AFE) 22, the signal can be digitized in an analog to digital (A/D) converter 28 and then subjected to appropriate gain control (which may include compression) in an automatic gain control (AGC) unit 29. After appropriate gain control, the signal can be divided into n analysis channels 30, each of which includes at least one bandpass filter, BPFn, centered at a selected frequency. The signal present in each analysis channel 30 is processed as described more fully in the U.S. Pat. No. 6,219,580, or as is appropriate, using other signal processing techniques and the signals from each analysis channel may then be mapped, using mapping function 41, so that an appropriate stimulus current of a desired amplitude and timing may be applied through a selected stimulus channel to stimulate the auditory nerve.

The exemplary system of FIG. 2B provides a plurality of analysis channels, n, wherein the incoming signal is analyzed. The information contained in these n analysis channels is then appropriately processed, compressed and mapped in order to control the actual stimulus patterns that are applied to the user by the ICS 21 and its associated electrode array 48.

The electrode array 48 includes a plurality of electrode contacts 50, 50', 50" and labeled as, E1, E2, . . . Em, respectively, which are connected through appropriate conductors to respective current generators or pulse generators within the ICS. Through these plurality of electrode contacts, a plurality of stimulus channels 127, e.g., m stimulus channels, may exist through which individual electrical stimuli can be applied at m different stimulation sites within the patient's cochlea or other tissue stimulation site.

It can be common to use a one-to-one mapping scheme between the n analysis channels and the m stimulus channels 127 that are directly linked to m electrodes 50, 50', 50", such that n analysis channels=m electrodes. In such a case, the signal resulting from analysis in the first analysis channel may be mapped, using appropriate mapping circuitry 41 or equivalent, to the first stimulation channel via a first map link, resulting in a first cochlear stimulation place (or first electrode). Similarly, the signal resulting from analysis in the second analysis channel of the SP may be mapped to a second stimulation channel via a second map link, resulting in a second cochlear stimulation place, and so on.

In some instances, a different mapping scheme may prove to be beneficial to the patient. For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites.

The "in-between" site at which a stimulus is applied may be referred to as a "stimulation site" produced by a virtual electrode. Advantageously, this capability of using different mapping schemes between n SP analysis channels and m ICS stimulation channels to thereby produce a large number of virtual and other stimulation sites provides a great deal of flexibility with respect to positioning the neural excitation areas precisely in the cochlear place that best conveys the frequencies of the incoming sound.

As explained in more detail below in connection with FIGS. 3A and 3B, through appropriate weighting and sharing of currents between two or more physical electrodes, it is possible to provide a large number of virtual electrodes between physical electrodes, thereby effectively steering the location at which a stimulus is applied to almost any location along the length of the electrode array.

The output stage of the ICS 21 which connects with each electrode E1, E2, E3, . . . Em of the electrode array may be as described in U.S. Pat. No. 6,181,969, incorporated herein by reference. Such output stage advantageously provides a programmable N-DAC or P-DAC (where DAC stands for digital-to-analog converter) connected to each electrode so that a programmed current may be sourced to the electrode or sunk from the electrode. Such configuration allows any electrode to be paired with any other electrode and the amplitudes of the currents can be programmed and controlled to gradually shift the stimulating current that flows from one electrode through the tissue to another adjacent electrode or electrodes, thereby providing the effect of "shifting" the current from one or more electrodes to another electrode(s). Through such current shifting, the stimulus current may be shifted or directed so that it appears to the tissue that the current is coming from or going to an almost infinite number of locations.

Additional features of the cochlear implant system shown in FIG. 2B involve the rate of electrical stimuli. The system shown in FIG. 2B can allow the current stimuli to be applied to the target tissue at fast rates and in a way that more naturally elicits a stochastic firing of the target tissue, as taught, e.g., in U.S. patent application Ser. Nos. 10/218,645 and 10/218,616, both of which were filed on Aug. 13, 2002, 60/425,215, filed on Nov. 8, 2002, and International Patent Application Serial No. PCT/US01/25861, filed on Aug. 17, 2002. All of these applications are assigned to the same assignee as the present application, and all are incorporated herein by reference.

Figure 3A:
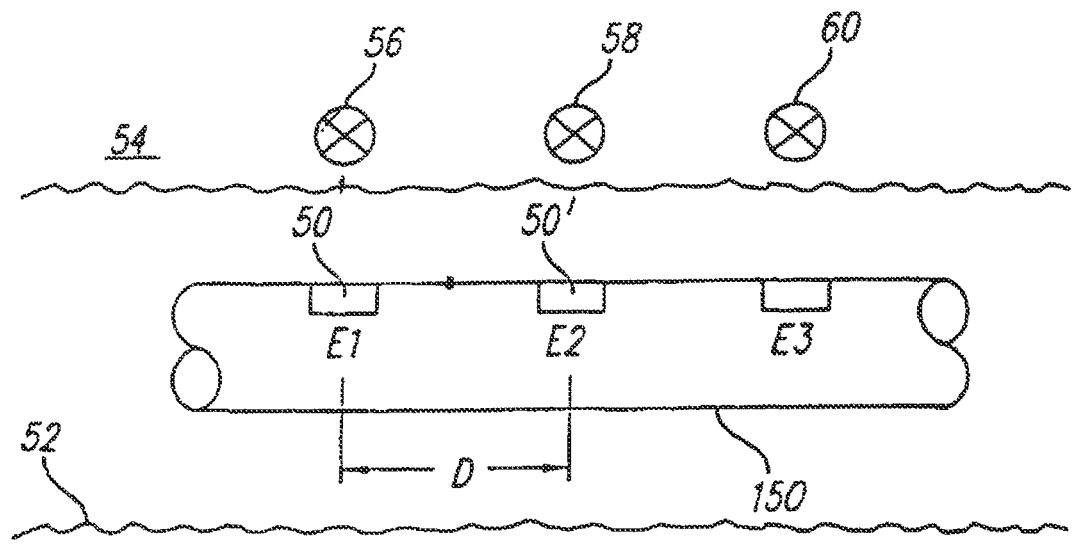
FIG. 3B schematically illustrates the locations of applied stimuli within a duct of the cochlea or other implanted location, with the benefit of virtual electrodes.

Next, with reference to FIG. 3A, a diagram is presented to illustrate the location where a stimulus is applied when virtual electrodes are employed. In FIG. 3A, three electrodes E1, E2 and E3 of an electrode array are illustrated. A reference electrode, not shown, is also presumed to be present some distance from the electrodes E1, E2 and E3, thereby allowing monopolar stimulation to occur between a selected one of the electrodes and the reference electrode. Bipolar stimulation could likewise occur, e.g., between electrodes E1 and E2, between E2 and E3, or between any other pair of electrodes.

The electrodes E1, E2 and E3 are located "in line" on a carrier 150, and are spaced apart from each other by a distance "D". Each electrode is electrically connected to a wire conductor (not shown) that is embedded within the carrier 150 and which connects the electrode to the ICS 21 (see FIG. 2A or 2B). The carrier 150 is shown inserted into a duct 52 within tissue 54 that is to be stimulated. For a cochlear implant system, the duct 52 typically comprises the scala tympani of a human cochlea.

When a stimulus current is applied to electrode E1, the stimulus location in the tissue 54 is essentially the location 56, adjacent the physical location of the electrode E1. Similarly, when a stimulus current is applied to electrode E2, the stimulus location in the tissue 54 is essentially the location 58, adjacent the physical location of the electrode E2. Likewise, when a stimulus current is applied to electrode E3, the stimulus location in the tissue 54 is essentially the location 60, adjacent the physical location of the electrode E3. It is thus seen that the resolution or precision, with which a stimulus may be applied to the tissue is only as good as is the spacing of the electrodes on the electrode array. That is, each stimulus location in the tissue 54 is separated by approximately the same distance "D" as separates the electrodes.

Figure 3B:
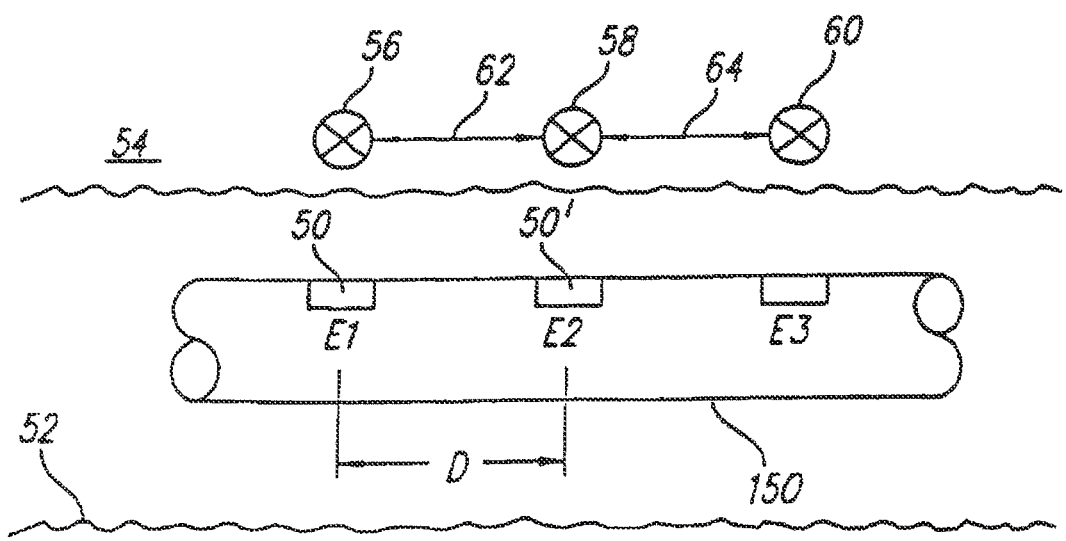

With reference to FIG. 3B, a diagram is presented to illustrate the location where a stimulus is applied when virtual electrodes are employed, specifically by using current steering. The structure of the electrode array and spacing between electrodes E1, E2 and E3 is the same as in FIG. 3A. Thus, when a stimulus current is applied only to electrode E1, the stimulus location in the tissue 54 is the location 56, the same as was the case in FIG. 3A. Similarly, when a stimulus current is applied only to electrode E2, the stimulus location in the tissue 54 is the location 58. Likewise, when a stimulus current is applied only to electrode E3, a stimulus location in the tissue 54 is the location 60. However, through application of current steering, a stimulus current may be shared, e.g., between electrodes E1 and E2 (and some other paired or reference electrode), and the effective tissue location where the stimulus is directed may be anywhere along the line 62 between points 56 and 58. Alternatively, if the current is shared between electrodes E2 and E3, the location in the tissue where the stimulus is directed may be anywhere along the line 64 between points 58 and 60.

To illustrate further, suppose a stimulus current having an amplitude I1 is applied to the tissue through electrode E1 (and some reference electrode). The location within the tissue 54 where the stimulus would be felt would be the point 56. However, if a stimulus current of only 0.9×I1 were applied through electrode E1 at the same time that a stimulus current of 0.1×I1 where applied through electrode E2, then the location within the tissue 54 where the stimulus would be felt would be a little to the right of the point 56, more or less somewhere on the line 62. If the stimulus current applied through electrode E1 continued to be deceased while, at the same time, the current applied through electrode E2 were increased, then the location in the tissue where the stimulus would be directed would move along the line 62 from left to right, i.e., from point 56 to point 58.

Similarly, by concurrently delivering current stimuli at electrodes E2 and E3, the location in the tissue where the effective stimulus would be felt would lie somewhere along the line 64, depending on the weighting of stimulus currents delivered at the two electrodes. This concept of current steering is described more fully in U.S. Pat. No. 6,393,325, incorporated herein by reference.

It is noted that the concept of virtual electrodes which directs a stimulus to a location on the cochlear location or place is broad concept. One method of implementing virtual electrodes is by concurrently delivering stimuli at two or more electrodes. Another way of implementing virtual electrodes is to present alternating stimuli at two electrodes in a time-multiplexed manner. For example, a first stimulus current is presented at the first electrode, then a second stimulus current is presented at the second electrode then, the first stimulus current is presented at the first electrode, then second stimulus current is presented at the second electrode, and so on, in a time multiplexed sequence. The first and second stimulus signals are usually different, e.g., they have different amplitudes and pulsewidths. Such delivery of stimulation will be perceived as if a virtual electrode were delivering a stimulus, which virtual electrode appears to be located between the two physical electrodes.

Figure 4:
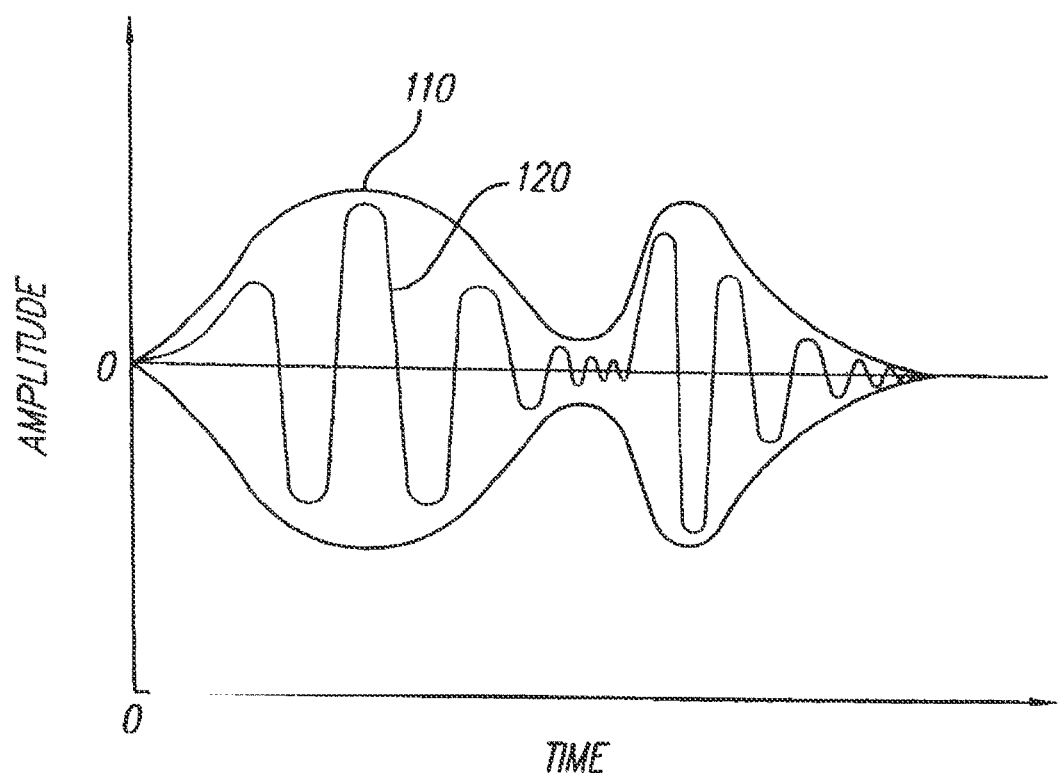
FIG. 4 shows a representation of sound wave amplitudes as a function of time and a slowly moving envelope.
Figure 5A:
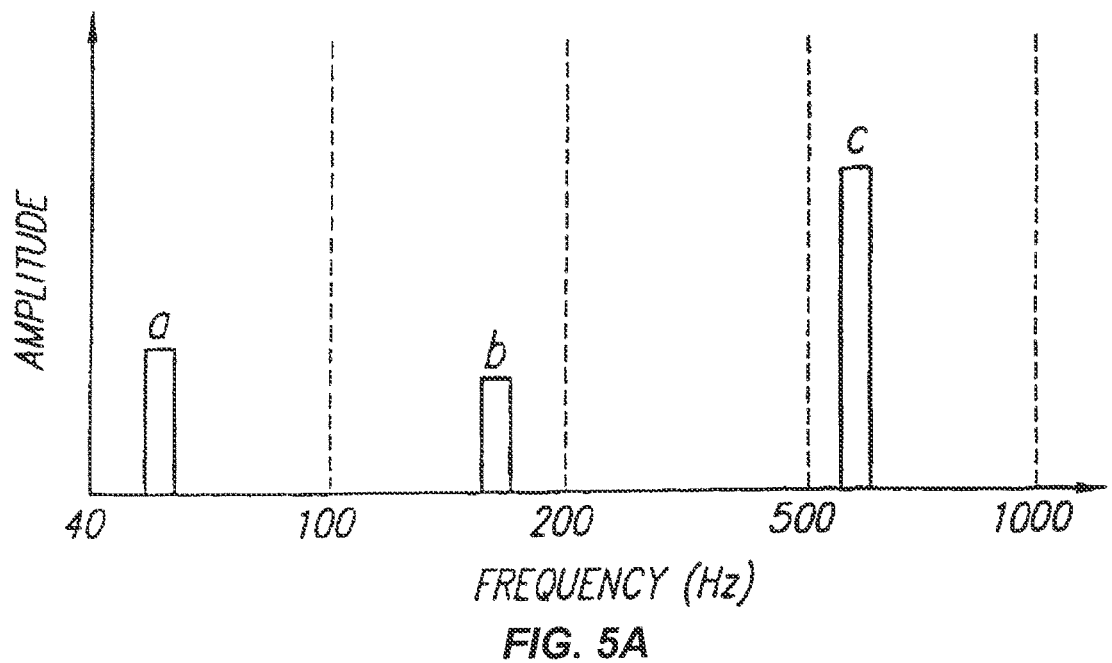
FIG. 5A shows a graph depicting four frequency bands or windows with dominant FTS components a, b, and c.
Figure 5B:
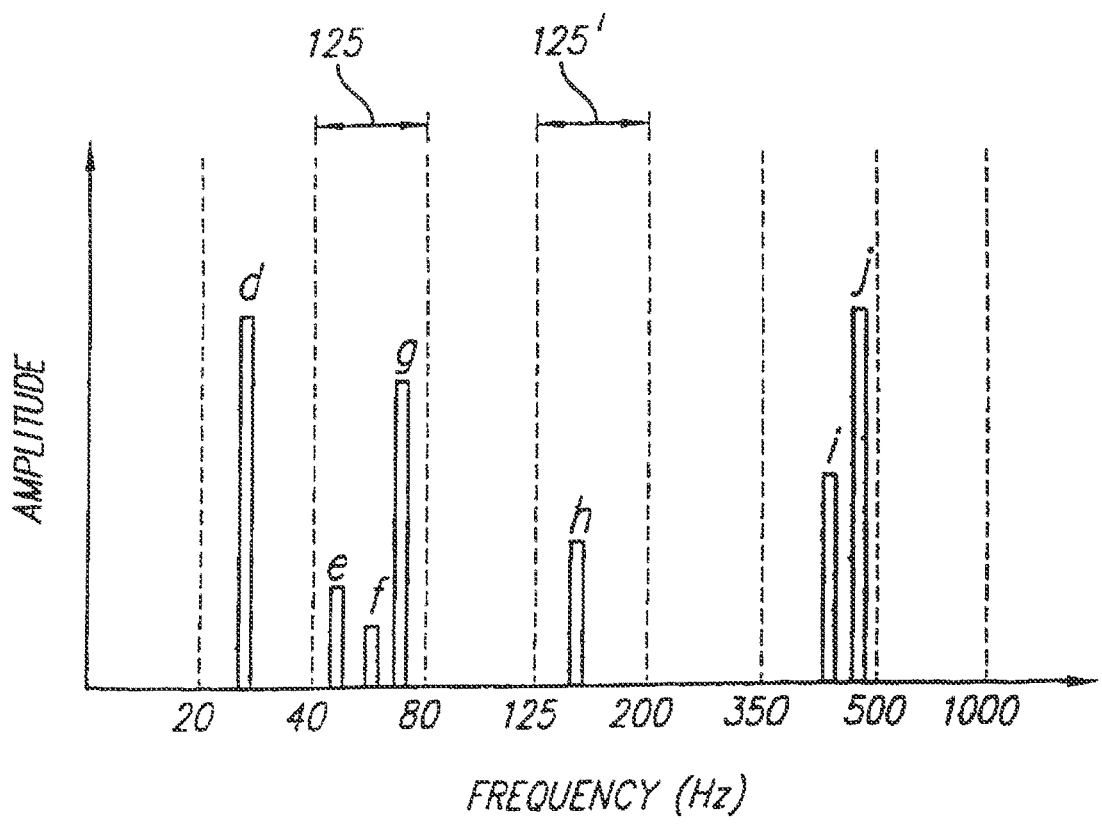
FIG. 5B shows a graph depicting eight frequency bands or windows with dominant FTS components d, g, h, and j.

FIG. 4 shows a representation of incoming sound waves as a function of time that could be picked up by microphone 18 as shown in FIG. 2B. The envelope 110 of the sound provides the slow moving or lower frequency components of the sound. The faster varying components 120, within this envelope 110 of the incoming sound are FTS (fine time structure) components of the sound. The incoming sounds, as represented in FIG. 4, may be deconstructed into frequency bands as shown in FIGS. 5A and 5B. These frequency bands may correspond to bandpass filters $BPF_1 \ldots BPF_n$ shown in FIG. 2B.

FIG. 5A provides an example in which incoming sounds are processed into four separate frequency bands, shown as 40-100 Hz, 100-200 Hz, 200-500 Hz, and 500-1000 Hz. The four frequency bands may represent four distinct stimulation channels, in the instant where n analysis channels=m stimulation channels. To implement the four channel processing (without the use of virtual electrodes0, at least four stimulating electrodes are required to convey the necessary stimuli to the cochlea. The dominant FTS components, a, b, and c occur in three of four frequency bands shown. Minor peaks may be present but are not illustrated here, as they are ignored in processing. The third frequency band does not show any activity.

To convey the identified, dominant FTS in each band, the stimulation system delivers stimulation pulses to three of four electrodes that are placed on the cochlea. The specific amplitudes of each dominant FTS component that is translated to stimulus pulses through the appropriate three of the electrodes can be translated as a perceived sound intensity. This perceived sound intensity can be increased by increasing the stimulation amplitude of a pulse such that more nerve fibers are recruited (captured) at one time. In addition, the frequency of the train of pulses delivered at the electrode can also be increased to recruit more nerve fibers within a fixed time interval. Such an increase in pulse frequency and amplitude can translate to an increase in perceived sound intensity.

FIG. 5B provides another example of an eight-channel system in which the sound frequency spectrum, from 0 Hz to 1 kHz, is divided into eight frequency bands 125, 125'. Dominant FTS components within each frequency analysis band 125, 125' shown are d, g, h, and j. These dominant FTS components are identified, selected and captured by the cochlear stimulation system. Minor peaks e, f and i are discarded or are not identified. In such an eight-channel system (where n analysis channels=m stimulation channels), there should be at least eight electrodes in the electrode array, each electrode 50, 50', 50" representing one analysis channel 30. As illustrated in FIG. 5B, when the sound spectrum is broken into more frequency bands to capture more FTS, the resolution of the stimulation system is enhanced because it will be able to capture smaller components such as e and f. Thus, it can be appreciated that higher resolution can be obtained by having more analysis channels ($BPF_1 \ldots 8PF_N$), for example, using sixteen different channels employing a sixteen electrode array 48. On the other hand, there is a practical limit to increasing the number of frequency analysis bands that can be used in a cochlear stimulator because of space and power limitations of the device.

It is important to understand however, that even in a system having many analysis channels, e.g., sixteen, there is a loss of FTS information because, while the dominant FTS component, for instance, g, shown in FIG. 4B, is identified within a single frequency band (40-80 Hz), the conventional stimulation system does not further attempt to convey the exact frequency of the FTS component within that band. Rather, it is conveyed generally by the fixed position of an electrode that represents that particular frequency band. It is assumed that the dominant frequency is centered and fixed somewhere in the middle of an analysis frequency band (or band-pass frequency). This limitation is inherent in any conventional cochlear stimulation systems because each electrode is placed in a fixed location with respect to the electrode array and, when the array is implanted, each electrode is fixed with respect to the cochlea. As a result, FTS frequency information is lost.

Figure 6A:
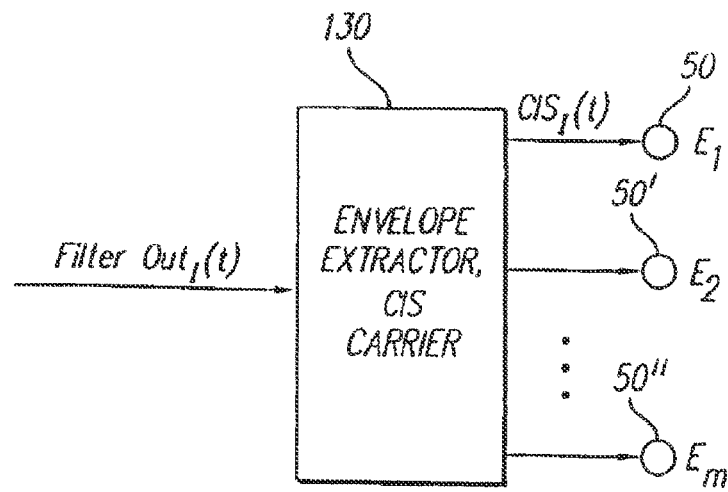
FIG. 6A shows a block functional diagram representing conventional sound processing in a cochlear implant using an envelope extractor.

FIG. 6A shows a partial block diagram of the processing system and method that are presently practiced in conventional cochlear stimulation systems and can be used to illustrate how FTS is lost. The concept of virtual electrodes is not employed in a conventional system. After filtering out the dominant frequency components in each frequency band using an envelope extractor, as shown by the rectangular box 130, the dominant frequency component is conveyed to the respective electrode 50, 50', 50" that corresponds to that particular frequency band. It can be seen that the position of a dominant frequency, for example, component c in FIG. 5A will be positioned on the cochlea, spectrally in the middle of the frequency band between 500 Hz to 1000 Hz, instead of closer to the 500 Hz as shown.

Figure 6B:
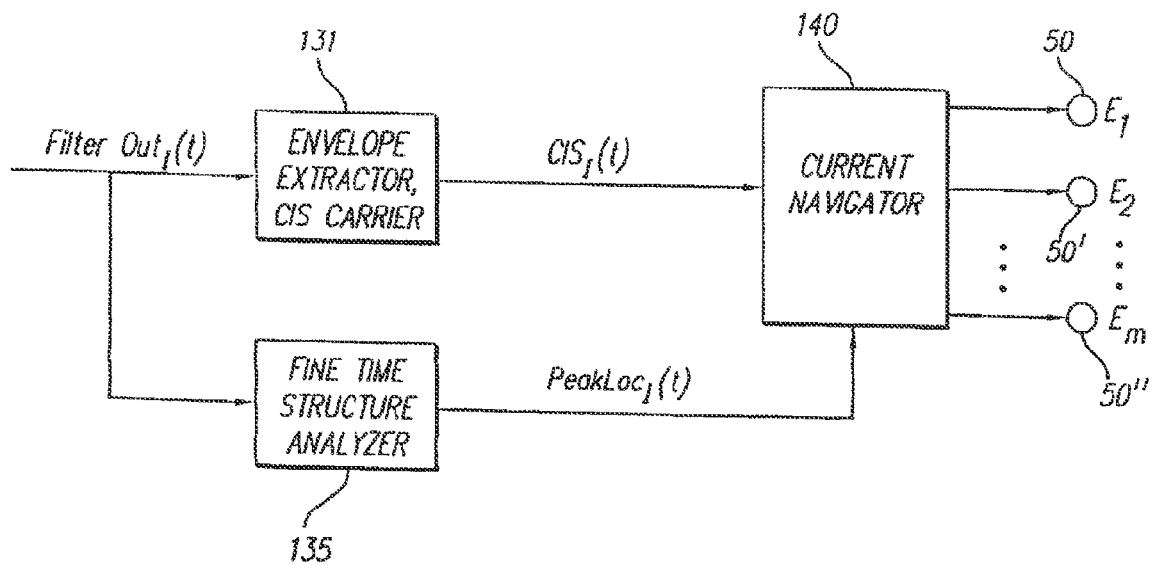
FIG. 6B shows a block functional diagram representing a system and method in accordance with one aspect, which includes an FTS analyzer/estimator and a current navigator.

The block diagrams of FIGS. 6A and 6B show that both the conventional cochlear stimulator system and the system of the present invention includes an envelope extractor 130 and 131 for providing the carrier signal, and a linear array of m electrodes, $E_1, E_2 \ldots E_m$, which are represented as 50, 50', and 50", respectively.

FIG. 6B shows, in accordance with the present invention, a block diagram of a cochlear stimulation system, which captures the FTS information in the auditory stimulation signals and conveys this information spatially (spectrally) to the nerves in the cochlea. The system shown in FIG. 6B includes: (a) an envelope extractor 131; (b) a fine time structure (FTS) analyzer/estimator 135; and (c) a current navigator 140 for creating virtual electrodes in order to precisely direct stimuli to various spatial locations (the place) on the cochlea that correspond to the FTS captured and analyzed by the FTS analyzer 135. The task of the FTS analyzer 135 is to precisely estimate the dominant FTS components in each frequency band as, for example, shown previously in FIG. 6B.

Assuming a stimulation system, which has eight analysis frequency bands, the FTS analyzer 135 determines the dominant FTS component within each analysis frequency band. The dominant FTS component within each band is identified, including the dominant component's precise frequency within the band. The other minor FTS components within a frequency band (such as inferior components e and f, in FIG. 5B) can be discarded.

The obtained FTS is then linearly added to the carrier signal obtained from the envelope extractor 131 by the current navigator 140 which processes and spatially directs the presentation of stimuli on the various cochlear places via one or more electrodes 50, 50', 50" such that the peak of the stimulation will be presented more precisely at the cochlear locations (places) that correspond to the FTS dominant frequency components in each frequency band.

Figure 7:
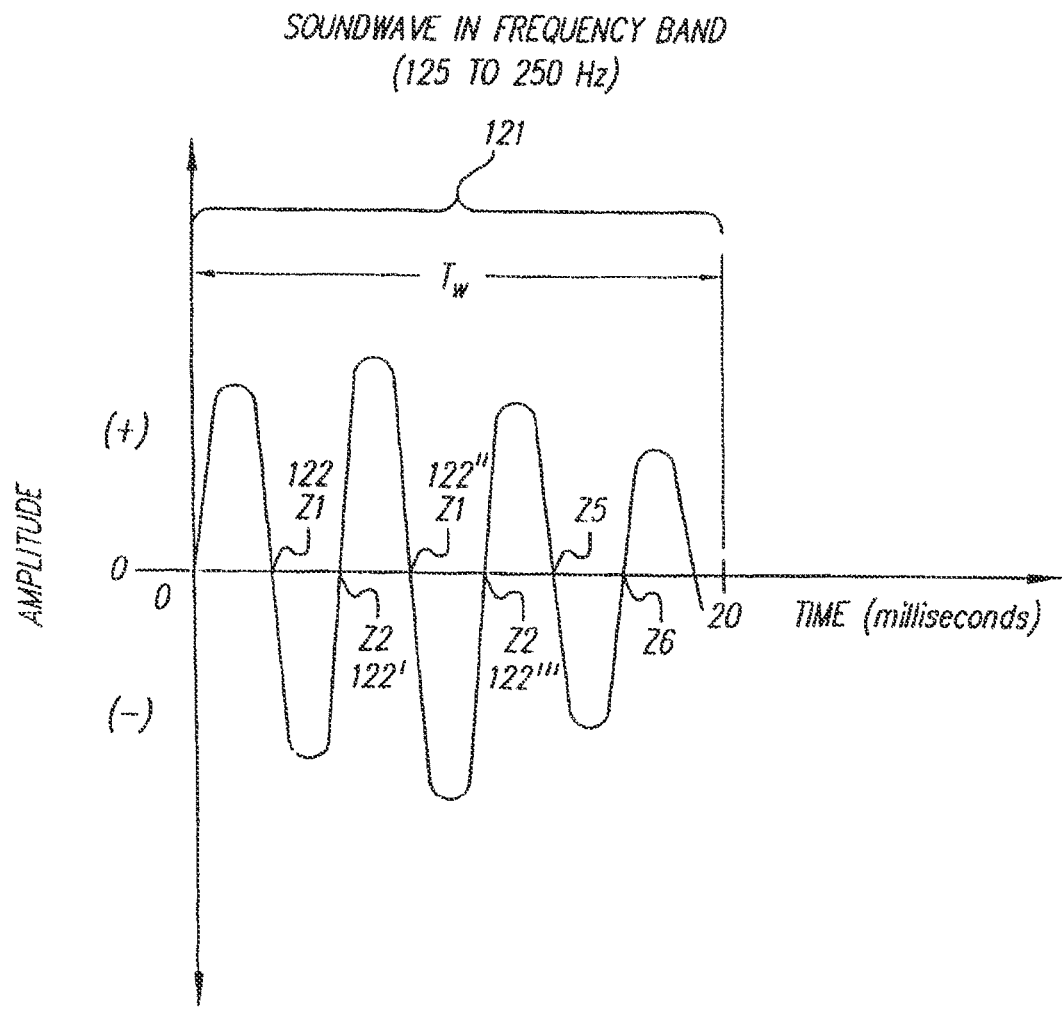
FIG. 7 depicts a filter output, which is one frequency band, wherein the dominant FTS frequency component is calculated by averaging the intervals between zero crossings of a waveform or counting the number of zero crossings of a waveform and averaging the result.

FIG. 7 shows a graph, in accordance with the present invention, one method for determining the dominant FTS component (the precise frequency) within a frequency band. The graph shows a sampled time window, $T_w$, 121 of 20 milliseconds sampling sounds within a single frequency band of 125 to 250 Hz. The dominant FTS component within this frequency band can be calculated by averaging the time intervals between successive zero crossings, 122, 122', 122" also labeled in FIG. 6 as Z1, Z2, Z3, Z4, Z5 and Z6 within a time window, $T_w$, illustrated here as 20 milliseconds. The peak FTS estimate is simply 1 over the averaged intervals of time between successive zero crossings. For example, the intervals of time are represented by the time between Z2 and Z1; the time between Z3 and Z2, the time between Z4 and Z3, the time between Z5 and Z4 and the time between Z6 and Z5. Although the example shows a time window, $T_w$ of 20 milliseconds, a time window of between about 10 to 100 milliseconds may be used to smooth the estimate so that stimulation is not perceived as noisy. Another, alternative embodiment of the present method for determining the FTS of the dominant component is to count zero crossings of the sound waves in a predetermined time window. The number of zero crossings is divided by the total duration of the time window to achieve the frequency estimate. For instance, both positive and negative going crossings are counted (in this case seven), then the number of zero crossings is further divided by 2 and then divided again by the total duration of time, $T_w$, 121, which is 20 milliseconds. Sufficiently accurate estimates can be achieved with a time window, $T_w$, that is at least 10 milliseconds long and preferably between about 10 to 100 milliseconds.

Still another alternative method of the present invention for determining the dominant FTS component is somewhat more sophisticated and employs a Fast Fourier Transform to precisely de-construct the fundamental frequency components in a particular incoming sound. The dominant FTS component in a frequency band should be sustained over a time duration of about between 10 to 100 milliseconds. A formant tracker, which can identify the dominant FTS components in a frequency band can be employed. A hardware and software implementation that uses a Fast Fourier Transform may, however, may require greater processing power and, therefore, use more energy and use up more device space compared to the simple method described which needs only detection and counting of zero crossings.

Although fine time structures have been found to be essential for representing musical melodies, the above methods do not take into account the recent findings that non-simultaneous stimulation of nearby physical or virtual electrodes may be perceived as a single pitch. For example, if in one band, the desired stimulation location is that corresponding to 1000 Hz, and in the adjacent band the desired location corresponds to 1300 Hz, then if both are presented, the subject might perceive a pitch corresponding to 1150 Hz. This phenomenon is sometimes referred to as decreased resolution and occurs when one energy/frequency pair is within a "resolution region" of another energy/frequency pair. It has been found that when two or more energy/frequency pairs are within a resolution region of one another, they are harmonically unrelated. It has further been determined that when an interfering energy/frequency pair or sound signal component is removed, the remaining components or energy/frequency pairs are harmonically related and the individual perceives the distinct components rather than an unintended sound or pitch.

Figure 8A:
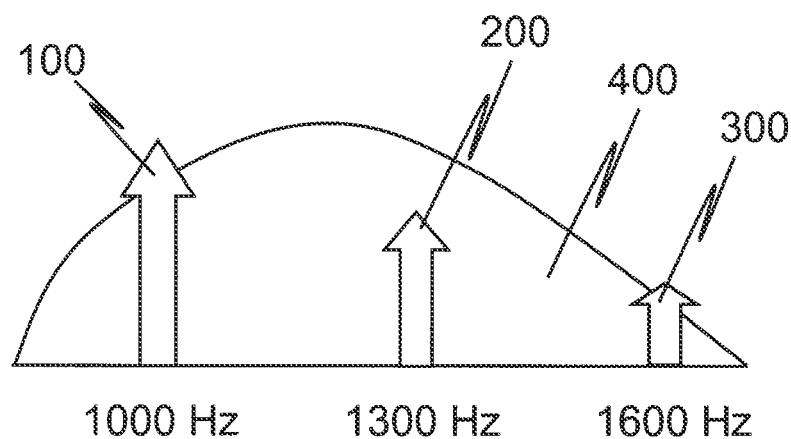
FIG. 8A presents a graphical depiction of perception of a sound having multiple frequency components that are within a resolution region.

Therefore, once the dominant FTS in each of the frequency bands are identified by one of the methods identified above, a determination must be made as to whether or not any two dominant FTS are within a resolution region, and how to minimize interference in the event that they are. FIG. 8A presents a graphical depiction of perception of a sound having multiple frequency components that are within a resolution region. In the example, the stimulus applied could be a FTS current-steered strategy as described above, or any other time domain strategy, frequency domain strategy, or other strategy that analyzes spectral peaks. The sound signal applied has three components 100, 200, and 300, each corresponding to a different frequency. Component 100 has a frequency of 1000 Hz. Component 200 has a frequency of 1300 Hz, and component 300 has a frequency of 1600 Hz. The perception of these separate pitches by a patient having a resolution region of approximately ⅓ octave or 300 Hz is depicted by the region 400 of the graph. As shown, the patient does not perceive three separate pitches associated with each of the three frequencies. Instead, the patient perceives a single pitch characterizing a frequency of somewhere between 1000 Hz and 1600 Hz, which is harmonically unrelated to the original frequencies or pitches.

Figure 8B:
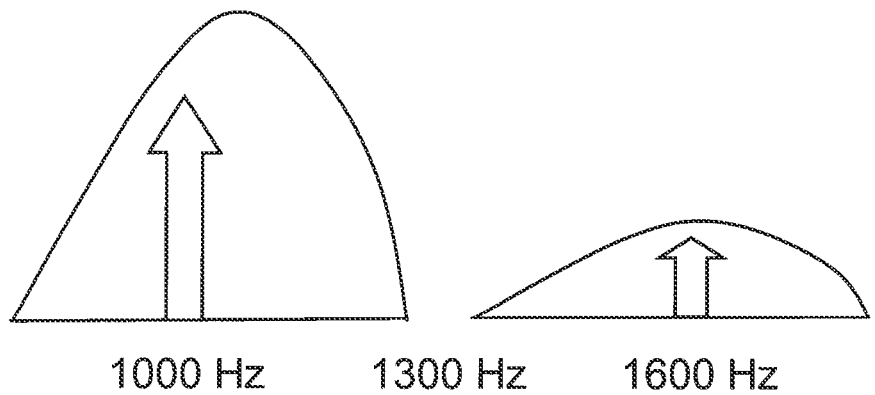
FIG. 8B presents a graphical depiction of perception of a sound in which the middle component of FIG. 4A has been removed.

FIG. 8B presents a graphical depiction of perception of a sound in which the middle component of FIG. 8A has been removed. This graph depicts a masked strategy in which the middle frequency has been masked or removed. The difference between the two frequencies (600 Hz) is greater than the resolution region (300 Hz). Therefore, the patient perceives two separate pitches; one associated with a 1000 Hz sound signal and another associated with a 1600 Hz sound signal. The two frequencies are harmonically related.

Figure 9:
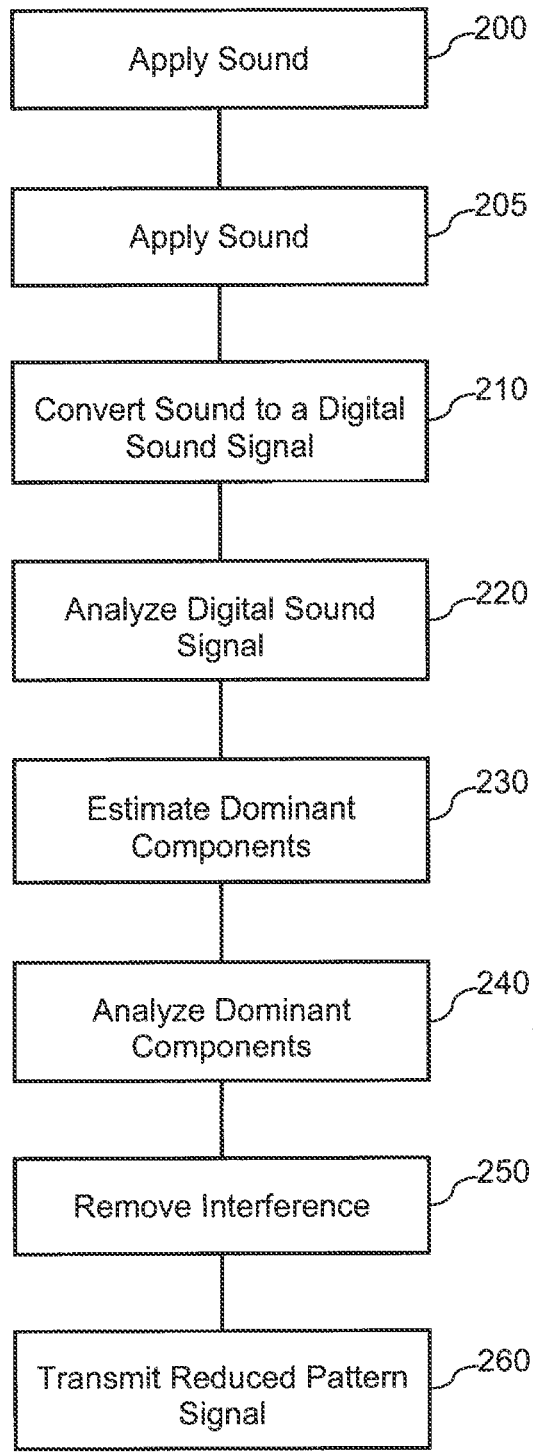
FIG. 9 presents a flowchart of a method for reducing the effects of decreased resolution in a cochlear implant.

FIG. 9 presents a flowchart of one method for reducing the effects of decreased resolution in a cochlear implant. Sound is generated and applied at 200. The sound signal is converted to an electrical signal at 205. This step can be performed by a microphone that senses sound waves and converts the waves to corresponding electrical signals, thus functioning as an acoustic transducer. For example, microphone 18 depicted in FIGS. 2A and 2B can perform step 200. An analog-to-digital converter, such as the converter 28 shown in FIG. 2B, associated with a cochlear implant implanted into a patient converts the electrical sound signal to a digital signal at 210. The signal is divided into frequency bands and analyzed at 220. An analyzer estimates the dominant components within each frequency band at 230. The dominant components are further analyzed at 240 to determine if any two components are within a resolution region of one another. This is accomplished by applying a patient-specific algorithm, which is derived by one or more psychophysical techniques, some of which are described further below. If two or more components are within a resolution region of one another, the component with less energy is masked (i.e., removed) at 250 with a masker. This step applies to any two of a potential multitude of components, thus removing one, two, three, four, or more components from the sound signal. An alternative to removing the component is to reduce the amplitude of the component using a masking function. The reduced pattern signal is then transmitted at 260 to the array of electrodes associated with the cochlear implant. Steps 220-260 are performed by a speech processor, such as the speech processor 16, depicted in FIGS. 2A and 2B.

Figure 10:
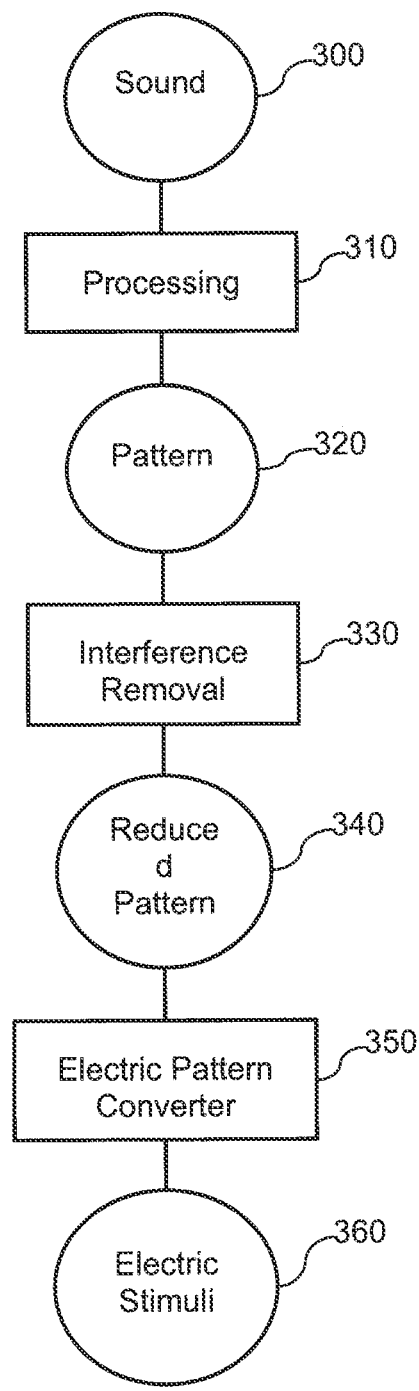
FIG. 10 presents another flowchart of a method for reducing the affects of decreased resolution in a cochlear implant.

FIG. 10 presents another flowchart of a method for reducing the effects of decreased resolution in a cochlear implant. Sound is generated at 300 and processed at 310 using anyone of a multitude of methods known to those of skill in the art, such as using a cochlear model, Fast Fourier Transformation (FFT) based phase and frequency determination, interval-based analysis of filter outputs, and Hilbert-based analysis of filter outputs. A pattern is generated at 320, which can include values for place, timing information, phase, amplitude, and width, which can represent descriptions of peaks of the spectra or the outputs of the analysis bands. The sound can also be resynthesized at this step to detect how much information is available and to determine the consequence of an implant. The pattern generated at 320 may be too detailed to present to the cochlear implant patient. This can be due both to constraints of the implant and/or, constraints of the physiology of the patient. Therefore, features of the pattern that would produce a sound most similar in pitch, loudness, and timbre to the original sound are selected at 330. For example, certain frequencies are removed. In particular, frequencies that are so close spatially to one another that they would merge if presented to the subject and produce the wrong pitch are removed at 330. A reduced pattern is subsequently generated at 340, again including values representative of, inter alia, cochlear place, timing information, phase, and amplitude. Again, the sound can be resynthesized as described with respect to step 320. The pattern is then ready to be converted into an electric signal at 350. In one embodiment, current-steering can be used to generate the desired pattern in the cochlea. Phase delays may be introduced here, and loudness balance would also be performed at 350. Finally, electric stimuli corresponding with the pattern generated at step 350 is transmitted via electrodes to the cochlea at 360.

Figure 11:
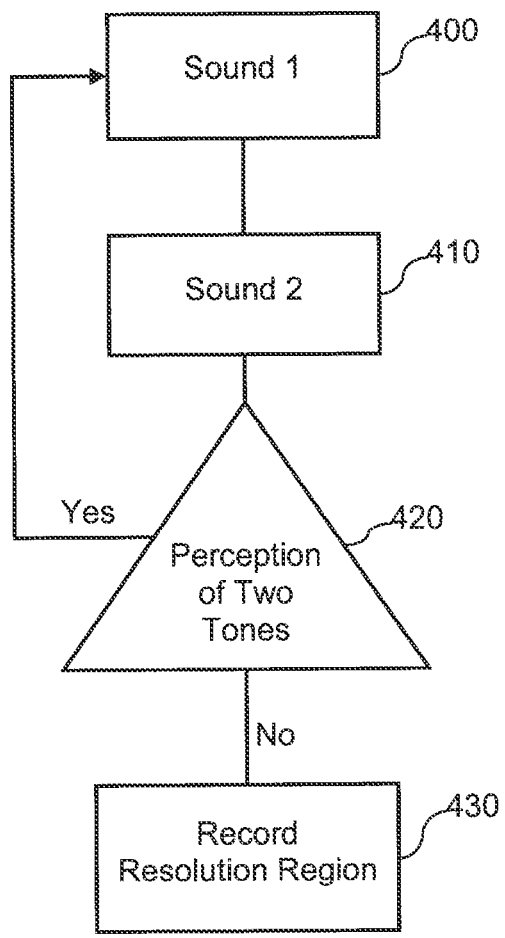
FIG. 11 presents a flowchart of a method for estimating a resolution region associated with a cochlear implant.

FIG. 11 presents a flowchart of a method for estimating the resolution region of an individual using the cochlear implants described herein. A first sound or tone is provided at 400. The first sound or tone has a predetermined frequency and is provided at time $T_1$. A second sound or tone is provided at 410. The second sound or tone is provided at a time $T_2$, which is close in time to $T_1$. Next, it is determined whether or not the individual hears or perceives two separate sounds at 420 by having the individual indicate if two separate sounds or tones are heard. If the individual has heard two separate sounds or tones, then the above steps are repeated until it is determined that the individual does not hear two separate sounds, wherein the second sound at 410 has a frequency closer to the frequency of the first sound at 400 upon each consecutive repetition of the above steps. When it is determined that the individual does not hear two separate sounds, the difference in frequency between the first and second sounds is recorded at 430. This is the estimate of the resolution region for the individual.

In another embodiment, sound 1 and sound 2 are provided by interleaving short pulse trains between two electrodes to provide a dual-sensation stimulus. The alternation rate can be larger than a predetermined value, such as 100 Hz. The resulting stimulus is compared to a sensation evoked by a single electrode near the middle of the two previously-stimulated electrodes and it is determined if the dual-sensation stimulus sounds like a multi-component stimulus as compared to the single electrode stimulus. In yet another embodiment, the method can be performed by heuristically adjusting the resolution region until optimal sound quality is achieved while listening to speech or simple music.

The estimated resolution region can be used to calibrate each cochlear implant to eliminate those sound components that interfere with one another. In this way, spectral resolution achievable by each individual or patient is explicitly taken into account.

Figure 12:
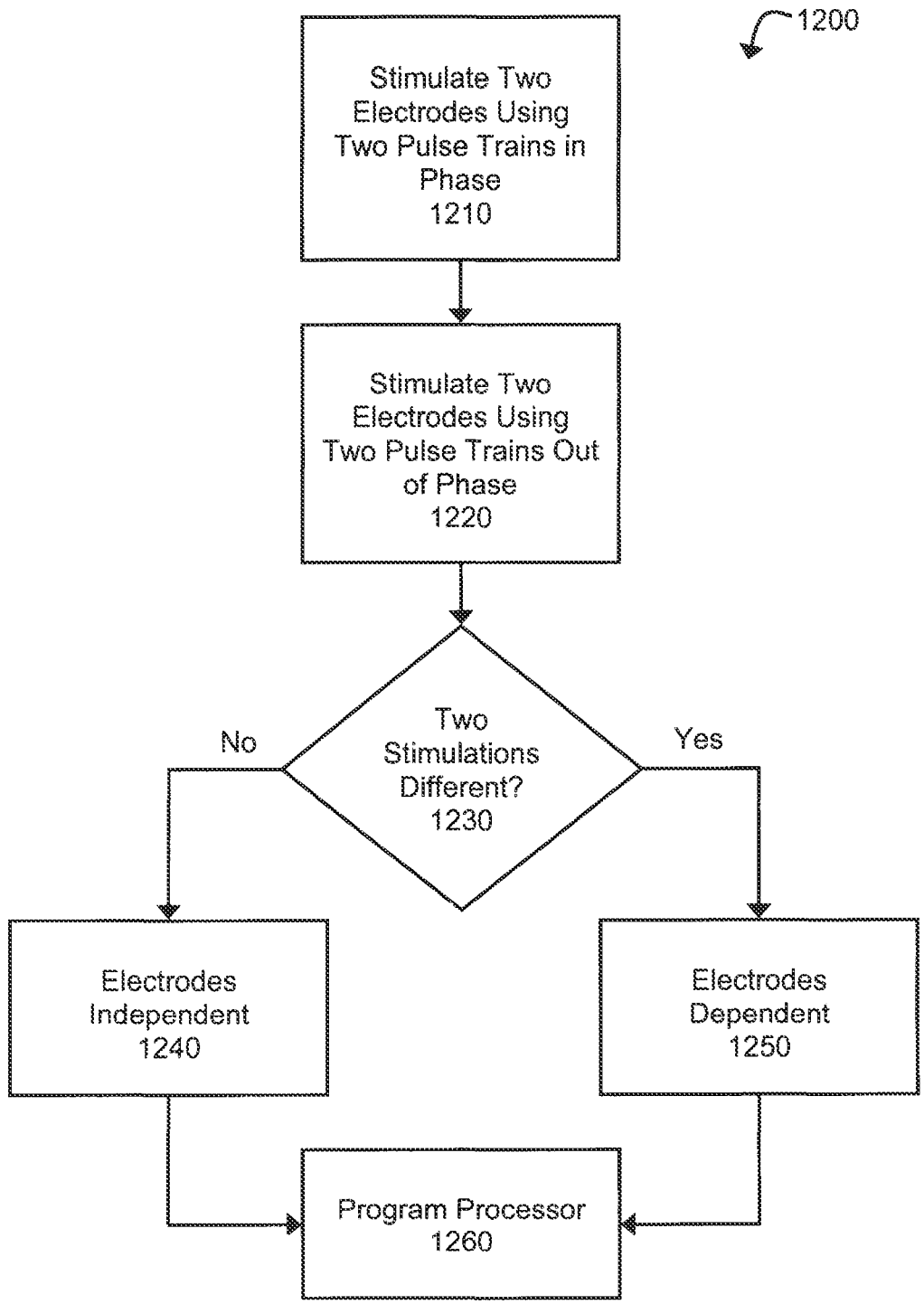
FIG. 12 presents a flowchart of a method of determining channel independence.

FIG. 12 illustrates another flowchart of a phase sensitivity test 1200 for estimating the resolution region of an individual using the cochlear implants described herein. The phase sensitivity test 1200 is used to determine whether any two components (electrodes) are within a resolution region (neural population) of one another. This is accomplished by applying a patient-specific algorithm, which is derived by one or more psychophysical techniques. When detected that two or more electrodes are within a resolution region of one another, the electrode with less energy is masked (i.e., removed or not stimulated) with a masker. Two or more electrodes from the electrode array can be tested, thus removing one, two, three, four, or more electrodes from the sound signal. An alternative to removing the electrode is to reduce the amplitude of the stimulating current applied using a masking function. The reduced pattern signal is then transmitted to the array of electrodes associated with the cochlear implant.

The phase sensitivity test 1200 involves stimulating a pair of electrodes selected from the electrodes 50 of the electrode array 48 associated with the cochlear implant. Stimulating the pair of electrodes includes applying a pulse train to each of the selected pair of electrodes. The stimulation rate is low (e.g. 100 Hz or lower). In one stimulation, a selected pair of electrodes is stimulated 1210 to provide two pulse trains that are temporarily adjacent (in phase). In another stimulation, the selected pair of electrodes is stimulated 1220 to provide two pulse trains that are interleaved (out of phase). For example, one stimulation can be applied with two pulse trains that have a phase difference of near "0" phase. And, another stimulation can be applied with two pulse trains that have a phase difference of "$\pi$". In some implementations, other phase differences can be used.

When the two pulse trains are in phase (near "0"), the rate of stimulation is not perceived to have changed. When the two pulse trains are out of phase, the rate of stimulation is essentially doubled. For a cochlear implant individual, the doubling of the rate of stimulation is more perceptually significant in the lower frequency than at a higher frequency. For example, the speech frequency range (e.g. up to 200 Hz) can be used.

A determination 1230 is made on whether the cochlear implant individual can differentiate between the two stimulations. In other words, a determination is made on whether the cochlear implant individual is sensitive to the delay or the phase difference. When the two stimulations are detected to be different, than the two channels are determined 1250 to stimulate the same neural population. In such instances, the two channels are deemed to be dependent. Alternatively, when the two stimulations are not detected to be different, then the two channels are deemed 1240 to stimulate different populations. In such instances, the two channels are independent.

Based on the phase sensitivity test 1200, the cochlear stimulation system 5 can be program to customize 1260 the cochlear stimulation strategy for each cochlear implant individual. In particular, the speech processor (SP) 16 can be programmed to define a customized stimulation strategy. In accordance with the customized stimulation strategy, the SP 16 generates appropriate control signals for controlling the ICS 21. In response to the control signals, the electronic circuitry within the ICS 21 applies a specified stimulation current to a selected pairs or groups of the individual electrodes included within the electrode array 48 associated with a cochlear implant. For example, the electrodes that are identified as being dependent may not be stimulated for one or more particular frames.

Figure 13:
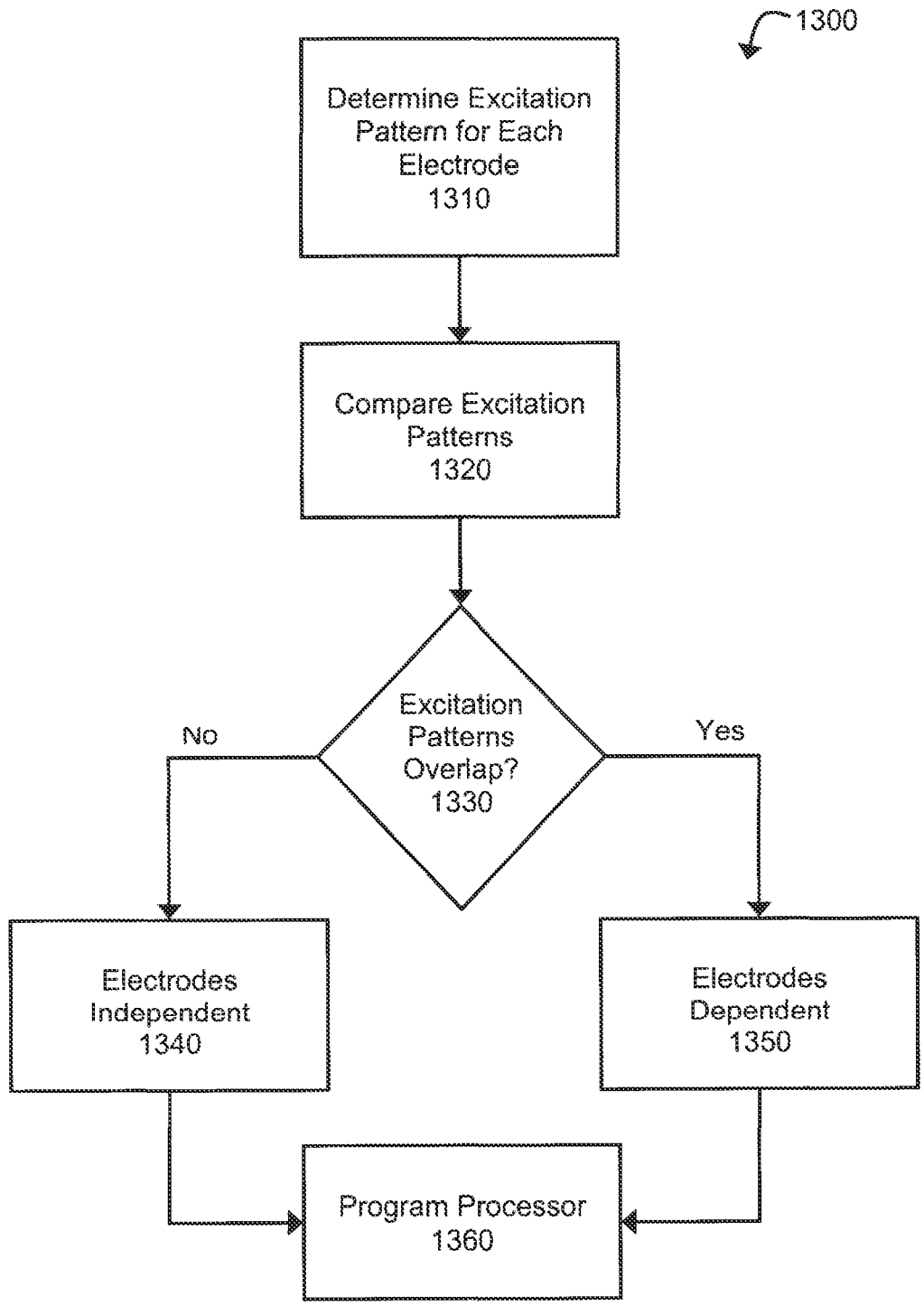
FIG. 13 presents a flowchart of another method of determining channel independence.

FIG. 13 illustrates a flow diagram of a forward masking test 1300 used to identify the independence of each channel in the cochlear implant. The forward masking test 1300 is a time-consuming test that can be used to directly derive excitation patterns for the electrodes. After deriving the excitation pattern for each electrode, the derived excitation patterns are compared to determine the amount of overlap among them. The amount of overlap between two or more excitation patterns (from two or more electrodes) can be used to determine the independence of the electrodes. For example, when detected that the excitation patters of two electrodes overlap, then the electrodes are deemed to be dependent. The electrodes are deemed independent when the excitation patterns do not overlap.

In the forward masking test 1300, the excitation pattern of interest is determined 1310 for each electrode by measuring a threshold to a probe stimulus that follows a stimulus of interest. For example, the cochlear implant individual is presented 1312 with three intervals of stimuli. All three intervals have the masker stimulus. Only one interval includes the probe and the masker. The individual is asked to identify 1314 the interval with the probe. When the individual correctly identifies the interval having the prove, the test is made harder by either increasing the current level (make louder) 1316 for the masker stimulus (psychophysical tuning curve) or decreasing the current level (make quieter) 1318 for the probe stimulus (forward masking pattern). The threshold for correctly identifying the probe stimulus is obtained 1319. For the case of the forward masking pattern, the threshold is compared to the threshold in isolation without any masking. Then you get the threshold shift. For psychophysical tuning curve, the threshold is compared to the masker alone.

The rate of stimulation for masker and probe is important and can be varied. In addition, the interval (time delay) between the masker and the probe is varied and the test repeated. While various time intervals between the masker and the probe are possible the interval in the range of 4-20 ms can be used. The average time interval can be about 10 ms.

The obtained excitation patterns for the electrodes are compared 1320 and the degree of overlap among the patterns is determined 1330. When a large overlap between two or more electrodes is detected, the overlapping electrodes are deemed dependent 1350. When little or no overlap is detected, the electrodes are deemed independent 1340. To provide the perception of a harmonic complex (several harmonics across the cochlea), independent peaks from stimulating independent electrodes are needed. When the electrodes are dependent, the cochlear implant individual does not perceive the harmonic complex. Instead, a masked sound is perceived.

The determined degree of independence for the electrodes is used to customize the cochlear stimulation strategy. In particular, the speech processor (SP) 16 can be programmed to define a customized stimulation strategy. In accordance with the customized stimulation strategy, the SP 16 generates appropriate control signals for controlling the ICS 21. In response to the control signals, the electronic circuitry within the ICS 21 applies a specified stimulation current to a selected pairs or groups of the individual electrodes included within the electrode array 48 associated with a cochlear implant. For example, the electrodes that are identified as being dependent may not be stimulated for one or more particular frames. The speech processor 16 and the ICS 21 can be combined as a fully implantable system.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer readable medium. The propagated signal is an artificially generated signal, e.g., a machine-generated electrical, optical, or electromagnetic signal, that is generated to encode information for transmission to suitable receiver apparatus for execution by a computer. The computer readable medium can be a machinereadable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed 20 across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and anyone or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, input from the user can be received in any form, including acoustic, speech, or tactile input.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

While the invention herein disclosed has been described by means of specific embodiments and applications thereof, numerous modifications and variations could be made thereto by those skilled in the art without departing from the scope of the invention set forth in the claims.

The invention claimed is:

1. A cochlear stimulation system comprising:
   a processor configured to generate one or more control signals based on a customized stimulation pattern in a cochlear implant implanted in an individual; and
   circuitry coupled to the processor, the circuitry configured to apply one or more stimulation currents to one or more selected electrodes of an electrode array associated with the cochlear implant based on the generated one or more control signals;
   wherein the customized stimulation pattern is determined based on a test that identifies independence of the one or more selected electrodes, and
   wherein the processor and the circuitry are further configured to conduct the test by performing operations that comprises:
      determining an excitation pattern for at least a first electrode and a second electrode selected from the array of electrodes by applying a masking stimulus and a probing stimulus separated by a time delay to each electrode, and determining an ability of the individual to distinguish the masking and probing stimuli; and
      comparing the excitation pattern for the first electrode against the excitation pattern for the second electrode.

2. The cochlear stimulation system of claim 1, wherein the processor is configured to determine the ability of the individual to distinguish the masking and probing stimuli by using a psychophysical method.

3. The cochlear stimulation system of claim 1, wherein the processor is further configured to compare the excitation pattern for the first electrode against the excitation pattern for the second electrode by determining whether the excitation pattern for the first electrode overlaps with the excitation pattern for the second electrode.

4. The cochlear stimulation system of claim 3, wherein the processor is further configured to generate a control signal that controls the circuitry to selectively not stimulate the first and second electrodes when detected that the excitation pattern for the first electrode overlaps with the excitation pattern for the second electrode.

5. The cochlear stimulation system of claim 1, wherein determining the excitation pattern for each of the first and the second electrodes comprises measuring a threshold to a probe stimulus that follows a stimulus of interest.

6. The cochlear stimulation system of claim 1, wherein the processor and the circuitry comprises a combined implantable system.

7. The cochlear stimulation system of claim 1, wherein the processor is further configured to selectively stimulate the one or more electrodes based on the comparison.

8. A method for customizing a stimulation strategy in a cochlear implant implanted in an individual comprising:
   determining an excitation pattern for at least a first electrode and a second electrode selected from an array of electrodes associated with the cochlear implant, wherein the determining comprises
      applying a masking stimulus and a probing stimulus separated by a time delay to each electrode, and
      determining an ability of the individual to distinguish the masking and probing stimuli; and
   comparing the excitation pattern for the first electrode against the excitation pattern for the second electrode.

9. The method of claim 8, wherein the ability of the individual to distinguish the masking and probing stimuli is determined using a psychophysical method.

10. The method of claim 8, wherein the comparing comprises determining whether the excitation pattern for the first electrode overlaps with the excitation pattern for the second electrode.

11. The method of claim 10, wherein the selectively stimulating comprises selectively not stimulate the first and second electrodes when detected that the excitation pattern for the first electrode overlaps with the excitation pattern for the second electrode.

12. The method of claim 8, wherein determining the excitation pattern for each of the first and the second electrodes comprises measuring a threshold to a probe stimulus that follows a stimulus of interest.

13. The method of claim 8, further comprising selectively stimulating one or more electrodes of the array of electrodes based on the comparison.

14. A non-transitory computer-readable medium on which are stored instructions comprising instructions that when executed cause a programmable device to customize a stimulation strategy in a cochlear implant implanted in an individual by performing operations comprising:
   determining an excitation pattern for at least a first electrode and a second electrode selected from an array of electrodes associated with the cochlear implant, wherein the determining comprises:
      applying a masking stimulus and a probing stimulus separated by a time delay to each electrode, and
      determining an ability of the individual to distinguish the masking and probing stimuli;
   comparing the excitation pattern for the first electrode against the excitation pattern for the second electrode; and
   selectively stimulating one or more electrodes of the array of electrodes based on the comparison.

15. The computer-readable medium of claim 14, further operable to cause the programmable device to determine the ability of the individual to distinguish the masking and probing stimuli based on a psychophysical method.

16. The computer-readable medium of claim 14, further operable to cause the programmable device to compare the excitation patterns to determine whether the excitation pattern for the first electrode overlaps with the excitation pattern for the second electrode.

17. The computer-readable medium of claim 16, further operable to cause the programmable device to selectively not stimulate the first and second electrodes when detected that the excitation pattern for the first electrode overlaps with the excitation pattern for the second electrode.

18. The computer-readable medium of claim 14, further operable to cause the programmable device to determine the excitation pattern for each of the first and the second electrodes by measuring a threshold to a probe stimulus that follows a stimulus of interest.

* * * * *